US011985961B2

(12) United States Patent
Ngo et al.

(10) Patent No.: US 11,985,961 B2
(45) Date of Patent: May 21, 2024

(54) DEVICE AND METHOD FOR BREEDING INSECTS

(71) Applicants: Gia Tien Ngo, Karlsruhe (DE); Rohi Shalati, Karlsruhe (DE)

(72) Inventors: Gia Tien Ngo, Karlsruhe (DE); Rohi Shalati, Karlsruhe (DE)

( * ) Notice: Subject to any disclaimer, the term of this patent is extended or adjusted under 35 U.S.C. 154(b) by 151 days.

(21) Appl. No.: 17/632,117

(22) PCT Filed: May 14, 2020

(86) PCT No.: PCT/DE2020/100419
§ 371 (c)(1),
(2) Date: Feb. 1, 2022

(87) PCT Pub. No.: WO2021/023327
PCT Pub. Date: Feb. 11, 2021

(65) Prior Publication Data
US 2022/0272954 A1    Sep. 1, 2022

(30) Foreign Application Priority Data
Aug. 5, 2019   (DE) ..................... 10 2019 121 102.6

(51) Int. Cl.
*A01K 67/033*   (2006.01)
(52) U.S. Cl.
CPC ................................. *A01K 67/033* (2013.01)
(58) Field of Classification Search
CPC .................................................. A01K 67/033
See application file for complete search history.

(56) References Cited

U.S. PATENT DOCUMENTS

| 10,405,528 | B2 | 9/2019 | Comparat et al. |
| 2017/0142945 | A1* | 5/2017 | Demetrescu ....... G01N 35/0099 |
| 2017/0360014 | A1* | 12/2017 | Hall .................... B65G 1/0492 |

(Continued)

FOREIGN PATENT DOCUMENTS

| JP | H09-172910 A | 7/1997 |
| WO | 2012/115959 A2 | 8/2012 |

(Continued)

OTHER PUBLICATIONS

Google Translation of applicant submitted JP H09172910 (Year: 1997).*

(Continued)

*Primary Examiner* — Monica L Perry
*Assistant Examiner* — Aaron M Rodziwicz
(74) *Attorney, Agent, or Firm* — Collard & Roe, P.C.

(57) ABSTRACT

A device for breeding insects includes: at least one stack of boxes, which is located on a chassis, and a gantry, the gantry at least having a supply module, a cleaning module, an upward vertical transport, a downward vertical transporter, an upper transverse transporter and a lower transverse transporter. A guide system, such as a rail guide, for the gantry moves the gantry to the at least two stacks of boxes. A conveying system, such as a conveyor belt, conveys boxes from and to the at least one stack of boxes for cyclical restacking, using the gantry, and supplying and cleaning of the insects within the boxes, within the at least one stack. Boxes are put into and removed from the at least two stacks of boxes using the conveying system and the gantry.

15 Claims, 7 Drawing Sheets

(56) References Cited

U.S. PATENT DOCUMENTS

| | | | |
|---|---|---|---|
| 2018/0055021 A1* | 3/2018 | Calis .................... | A01K 67/033 |
| 2018/0070566 A1* | 3/2018 | Comparat ............ | B65G 1/0407 |
| 2020/0146270 A1* | 5/2020 | Calis .................... | A01K 67/033 |
| 2020/0205369 A1* | 7/2020 | Calis .................... | A01K 1/0047 |
| 2020/0253176 A1* | 8/2020 | Fotiadis ................ | A23K 10/26 |
| 2020/0260685 A1* | 8/2020 | Slade ................... | A01K 29/005 |
| 2022/0007622 A1* | 1/2022 | Du Jonchay ......... | A01K 67/033 |
| 2022/0015327 A1* | 1/2022 | Clesse .................. | A01K 1/0064 |
| 2022/0061232 A1* | 3/2022 | Whelan ................. | B65G 1/065 |
| 2022/0304290 A1* | 9/2022 | De Gelder ........... | A01K 67/033 |
| 2022/0306404 A1* | 9/2022 | De Wolf ............... | B65G 47/19 |

FOREIGN PATENT DOCUMENTS

| | | |
|---|---|---|
| WO | 2014/171829 A1 | 10/2014 |
| WO | 2016/166471 A1 | 10/2016 |
| WO | 2017/007310 A1 | 1/2017 |
| WO | 2018/029597 A1 | 2/2018 |
| WO | 2019/053439 A2 | 3/2019 |

OTHER PUBLICATIONS

International Search Report in PCT/DE2020/100419, dated Sep. 30, 2020.

\* cited by examiner

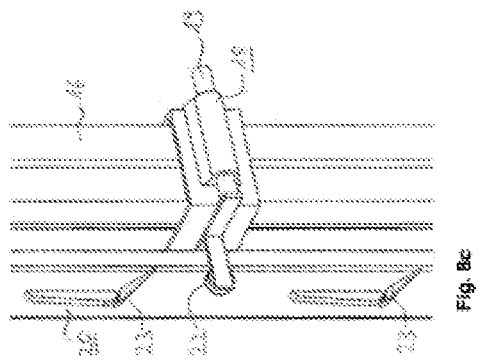
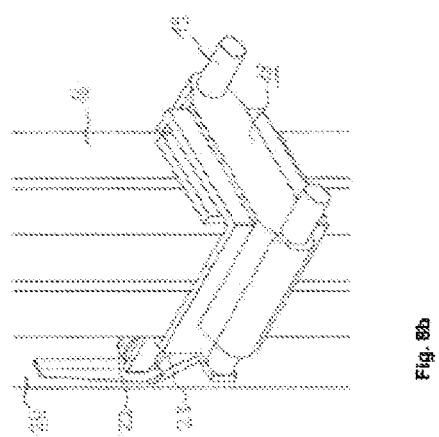
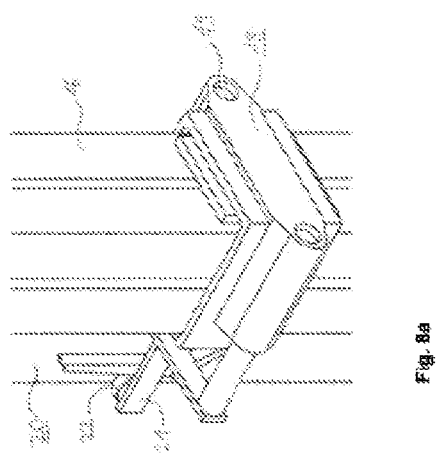

DEVICE AND METHOD FOR BREEDING INSECTS

CROSS REFERENCE TO RELATED APPLICATIONS

This application is the National Stage of PCT/DE2020/100419 filed on May 14, 2020, which claims priority under 35 U.S.C. § 119 of German Application No. 10 2019 121 102.6 filed on Aug. 5, 2019, the disclosure of which is incorporated by reference. The international application under PCT article 21(2) was not published in English.

BACKGROUND OF THE INVENTION

1. Field of the Invention

The invention relates to a device and a method for automated breeding, in particular of insects.

2. Description of the Related Art

From the prior art, inter alia WO 2019/053 439 A2 is known, said document relating mainly to a device for the recyclability of waste from insects as food for insect breeding, comprising, in this case, a waste module and a breeding module.

Furthermore, a device and a method for breeding insects for industrial series production of larvae from egg-laying mothers is known from the international patent application WO 2017/007310 A1. In this case, the device serves for breeding and producing larvae from egg-laying mothers, and in this case comprises an egg-laying region and a hatching region, which each comprise an individual food delivery system.

The international patent application WO 2014/171829 A1 also relates to a method and a device for breeding insects, a plurality of individual boxes being used. In this case, the method comprises the following steps:

Providing a plurality of boxes, filling at least some of the boxes of the plurality of boxes with a substrate which contains feed and insects in the immature state, as well as providing a climatic zone.

The method furthermore comprises a ventilation facility in which the plurality of boxes can be placed, providing a conveying system, and providing an observation system along the conveying system.

The method also includes providing a raw material supply station along the conveying system, and providing a ventilation system.

Furthermore, the known solution provides for periodic retrieval of at least one individual box of the plurality of boxes by the conveying system, from the climatic region, and a subsequent transfer of the box to the observation system.

The information relating to the substrate and the status of the insects in an individual box, obtained by the observation system, is evaluated and, on the basis thereof, instructions relating to the further breeding, harvesting or disposal of the insects in the individual boxes are issued.

A device for breeding larvae, comprising a plurality of culture dishes which are arranged in at least one stack of dishes, each stack comprising a plurality of planes of dishes, is known from the international patent application WO 2012/115 959 A2.

Each of said dishes contains an opening arranged at the top in order to be able to receive larvae and larvae food.

Furthermore, the device comprises a food dispensing system which is adapted such that the larvae food can be dispensed automatically and individually onto the respective dish. The device also contains a water supply system which is adapted such that the dishes can be automatically supplied with water.

The international patent application WO 2018/029597 A1 discloses a technological conveyor belt for breeding and/or rearing of non-flying insects and/or larvae of insects, which is characterized in that the conveyor belt is an autonomous conveyor belt having side walls arranged laterally on both sides, which are arranged lengthways on the conveyor belt, the top edge thereof being curved inwards at least once, having a bend angle of the edge of no less than 30°, preferably 30° to 90°. The conveyor belt further comprises cross members which generally perpendicularly support the lateral side walls of the conveyor belt and connect the opposing profiled side walls, the profiled side walls also being bearing structural elements.

The longitudinal edges of the conveyor belt and the lateral side walls together form a trough profile, the mass of the insects located on the surface of the conveyor belt, together with possible additional food and excrement of the insects, exerting pressure on the longitudinal edges of the conveyor belt and the lateral side walls, as a result of which the cross members as well as the profiled transverse side walls consist of a material having efficient heat-conducting properties.

Furthermore, an establishment for breeding insects is known from the international patent application WO 2016/166 471 A1. This contains a first zone in which the insects to be bred are stored in containers during their growth, and a second zone comprising at least one station which is designed such that it is possible to perform a breeding-related task for the insects in the containers. In this case, the containers of the first zone are combined in stacks, which are referred to as a base unit. The first zone thus comprises pallet rack in which the basic units are arranged. The first zone is furthermore equipped with an automated device which is configured such that the base unit can be moved between the first zone and in interface with the second zone.

SUMMARY OF THE INVENTION

Proceeding from this prior art, the object of the invention is that of providing a device and a method for automated breeding of insect larvae until they are ready for harvest. This object is achieved by a device for breeding and a method having the device hi accordance with the invention. Advantageous embodiments of the invention are discussed below.

The invention relates to a device for automated breeding, in particular of insects, comprising a plurality of individual boxes which can be arranged in a stack comprising a plurality of planes of boxes, said boxes being filled with larvae and substrate which contains inter alia food.

The device furthermore comprises an observation system by means of which information relating to the substrate and the status of the insects in each individual box can be obtained, such that instructions, in the form of further breeding, harvest or disposal of the insects in the individual boxes, can be output on the basis of said information. The device also comprises a food dispensing system which is adapted such that the food can be dispensed automatically and individually into the respective box.

The invention according to one aspect is characterized in that the device comprises at least one stack of boxes which is boated on a chassis, and a gantry. The gantry contains at least one supply module, a cleaning module, an upward vertical transporter, a downward vertical transporter, an upper transverse transporter, and a lower transverse transporter.

The device according to the invention furthermore provides for a guide system, in particular a rail guide, for the gantry to be present, such that the gantry can be moved towards at least one stack of boxes, and in that a conveying system is present, in particular a conveyor belt, it being possible for boxes to be conveyed from and to the at least one stack of boxes by means of the conveying system. It is also conceivable for the boxes conveyed by the conveying system to be able to be positioned by a positioning mechanism, in particular by means of lifting magnets, on the gantry, for loading and unloading by the relevant chassis.

As a result, cyclical restacking, and supplying and cleaning of the insects inside the boxes, within at least one stack, is made possible by means of the gantry, and boxes in the at least one stack of boxes can be loaded and unloaded by means of the conveying system and the gantry.

In an advantageous embodiment, the invention for the device provides for the gantry to be constructed from a profile system, in particular from a profile system made of aluminum, and/or from a welded structure. This is advantageous in that the gantry can be individually adapted to the size of the boxes and the height of the stack.

In a further advantageous embodiment, the invention for the device provides for the upward vertical transporter of the gantry opposingly, individually in each case, at least two drive units, containing a linear belt drive as well as at least two lifting fingers on each drive. These are loadable in the event of the upward movement of the upward vertical transporter, and can thus absorb weight, in particular the weight of a box. The lifting fingers can also be pushed outwards during insertion of a box from the conveyor belt through the passive chassis, from below, as a result of which the hooking and unhooking for the transport of the boxes, by the upward vertical transporter, can be carried out passively.

This is advantageous in that the upward vertical transporter contains just two movable parts, i.e. the linear belt drive and the lifting finger, as a result of which reduced mechanical wear can be achieved, and the maintenance of the upward vertical transporter is made easier.

According to another aspect, the invention for the device provides for the downward vertical transporter, located on the gantry, to comprise opposingly, individually in each case, at least two drive units, containing at least two linear belt drives as well as at least two lifting pin arms comprising at least two lifting pins connected to a roller, and a roller guide comprising deflection rockers.

Furthermore, the invention according to this aspect provides for the lifting pins of a lifting pin arm, which are connected to at least one roller, to be deflectable by the roller guide upon the downward movement of the downward vertical transporter, such that a box can be held and transported downward by means of said lifting pins.

In the case of the upward movement of the downward vertical transporter, the lifting pins connected to a roller can be deflected by at least one deflection rocker in the roller guide such that the downward vertical transporter can also be moved upward, without the lifting pins being extended in the process, and thus no box can be grasped.

A further box can also be received by means of a drive, for the downward movement of the downward vertical transporter, by the lifting pin arms and the lifting pins thereof connected to a roller, by means of the roller guide and the deflection rockers thereof.

This is advantageous in that a box can be both raised upward and conveyed downward by means of the downward vertical transporter.

This is achieved using just two movable parts, specifically a linear drive and the lifting pins of a lifting arm, which are connected to a roller, such that in this case too low mechanical stress and thus a long service life, as well as simple maintenance of the device, is ensured.

In another advantageous embodiment, the invention for the device provides for the transverse transporter above the gantry, to be achieved opposingly, individually in each case, by means of a linear belt drive, a lifting arm comprising at least two lifting receptacles, a roller on the lifting arm which is coupled by a linear shaft, and by means of a roller guide comprising at least two rockers. Furthermore, according to said advantageous embodiment the invention provides that, in the case of a movement of the lifting arm by a drive, in particular by means of a linear belt drive, comprising a roller, coupled by a linear shaft, along the roller guide, the lifting arm can be pivoted by means of a rocker on the roller guide, such that a box can be received and can be moved from left to right and/or from right to left.

The invention also provides, according to this advantageous embodiment, that a lifting arm can be deflected at a further rocker of the roller guide, by means of a roller fastened to the lifting arm by means of a linear shaft, such that a box can be deposited.

According to another aspect, the invention for the device provides for the transverse transporter below the gantry to provide, opposingly, individually in each case, a vertically oriented asymmetrical belt. This can be moved vertically by means of a horizontally oriented drive, the asymmetrical belt being of such a thickness, on one side, that a box can be grasped and moved from left to right and/or from right to left by means of a horizontally oriented drive, on account of the vertical movement of the asymmetrical belt. Thus, in this case too the lower transverse transporter is implemented by just two movable parts, the vertical drive and the asymmetrical belt, as a result of which the advantage of reduced mechanical wear and facilitated or reduced maintenance is achieved here too.

A further advantageous embodiment of the invention is characterized in that the gantry comprises servomotors, and hi that the active chassis contains a connection element, in particular a web, which is fastened to the Bowden cables that are fastened to the lifting fingers. The connection element can be actuated by the servomotors on the gantry such that the lifting fingers of the active chassis can be deflected outwards by actuation of the servomotors. As a result, a box ready for harvest can be unloaded onto a conveyor belt, through the active chassis, by means of the downward vertical transporter.

Here, too, the advantage is that the necessary movement of the active chassis is achieved by just one movable component, here, too, reduced wear of the mechanics being anticipated, as well as the associated lower maintenance costs of the device. It is also advantageous for the servomotors to be located on the gantry, since as a result it is not necessary for every active chassis to itself comprise servomotors, and thus a reduced use of material can be achieved, at a constant level of effectiveness, and the active chassis does not require its own power supply or separate actuation.

In a further advantageous embodiment, the gantry comprises a detection unit which comprises sensors, in particular heat sensors and humidity sensors, and/or a camera.

The parameters required for insect breeding, in particular humidity and temperature, which must prevail in a box for optimum breeding of insects, can be determined by means of the mentioned sensors and/or said detection unit.

In addition, images can also be captured by means of a camera, which images capture and reproduce the current state of the insects with supply materials in a box, it being possible for said captured images to be compared in each case with reference data stored in a database, such that the respective state of the insects with supply materials in a box can be determined, and the information thus obtained can be used for machine learning. Thus, the respective state of each individual box in at least two stacks can be determined by the detection unit of the gantry, by means of the device, resulting in the advantage that the optimal parameters for insect breeding can be monitored and adjusted.

According to a further aspect, the invention for the device according to the invention provides for the boxes in each case comprise a double base and at least one suction opening between the bases.

Furthermore, the upper base of the double base is formed as a grating-like base, such that waste, in particular feces, fall downward through said grating-like base.

Said feces can be removed or suctioned away by the cleaning module, through the suction opening between the double base.

This is advantageous in that impurities do not remain in the substrate, as a result of which it is possible to achieve a higher hygiene standard for the insects, and it can thus be expected that the insects do not, or barely, need to be treated with medication. Furthermore, the waste resulting from the insect breeding can be easily removed from the box via the double base and the suction opening, and can optionally be used further, for example in the form of fertilizer.

In a further advantageous embodiment, the invention contains a cleaning module which comprises at least two suction devices, it being possible for the waste to be suctioned through the suction opening of a box, between the double base, by means of at least one suction device, and the skins of the larvae as well as any food residues and other waste present inside the box can be suctioned out during the upward transverse transport, and/or taken up by means of electrostatics, and/or removed by means of air separation, by means of at least one second suction device.

According thereto, during the transverse transport of a box, by the transverse transporter above the gantry, from the upwards stack to the downwards stack, the cleaning module can remove both the waste from the double base of the box, and the skins and food residues of the larvae inside the box. As a result, a hygienic environment for the insects inside the box is ensured, as a result of which possible disease of the insects to be bred can be counteracted.

According to another aspect, the invention for the device provides for the supply module to be divided into at least two containers. Each of said containers comprises an individual metering roller in each case, such that in the event of transverse transport by the upper transverse transporter, first substrate and subsequently food can be dispensed, in the amount required in each case, into the relevant box, by means of the adjustable advancement of the metering roller of the relevant container.

In another advantageous embodiment, the invention for the device provides for the boxes to comprise an RFID chip or another passive electronic chip, and/or a barcode, and/or a 2D matrix, such that data, in particular state data of the boxes, can be stored and retrieved, as a result of which it is possible to carry out evaluations and, if necessary instructions, preferably automatically, on the basis of said data. This is advantageous in that information available on the chip, such as state data, number of the box, time within a stack, etc., can be read out and stored by means of a reader, in particular by means of a detection unit, as a result of which instructions, in particular unloading, cleaning of the box, or feeding of insects, can be carried out automatically, on the basis of said data.

In a further advantageous embodiment, the invention for the device provides for a station to be present for the gantry, in which the cleaning module can optionally be emptied, and in that the containers of the supply module can be refilled with the materials required in each case, in particular substrate and/or food. This therefore ensures further automation of the insect breeding.

According to another aspect, the invention for the device provides for the device according to an aspect of the invention, i.e. the at least two stacks of boxes comprising an active and a passive chassis in each case, and a conveyor belt under the active and passive chassis, and comprising a gantry having a rail guide, as well as according to the features of this aspect of the invention, can be lined up one behind the other, lengthways, as often as desired, it being possible for at least one gantry to move over all the stacks that are lined up lengthways.

Furthermore, according to the advantageous embodiment the invention provides that said devices lined up lengthways can be lined up side-by-side.

This is advantageous in that the device can be adapted to the respective local conditions, in particular the length, width and height of an industrial building, as a result of which optimum use can be made of the local conditions.

In another advantageous embodiment, the invention for the device provides for at least one conveyor belt to be arranged orthogonally on the devices described in this embodiment, such that said devices can be supplied with new boxes comprising insects and supply materials from a store, by means of said orthogonal conveyor belt.

The advantageous embodiment also includes the possibility of boxes ready for harvest being able to be transported away from the devices into a store, by means of said at least one conveyor belt that is oriented orthogonally with respect to the device described in this embodiment.

This is advantageous in that the transport and removal of new and ready-to-harvest boxes to and from devices takes place in a fully automated manner, by means of conveyor belts.

According to another aspect, the invention also provides a method in which the lowest box of the stack, in each case, which is located on the passive chassis, is raised, by at least one box height, by means of the upward vertical transporter. At the same time, the second box from bottom, from the stack of the active chassis, is raised by means of the downward vertical transporter, such that the lowest box of the stack is brought onto the active chassis by means of the lower transverse transporter, under the second raised by the upward vertical transporter.

The second from bottom box that is raised is also moved downward, by at least one box height, by means of the downward vertical transporter, the uppermost box of the stack, which is raised by one box height, by means of the upward vertical transporter, likewise being brought over the stack of boxes, located on the active chassis, by means of an upper transverse transporter.

During the transport of the box by means of the upper transverse transporter, the box comprising insects and the supply materials thereof is cleaned, and optionally equipped with corresponding supply materials, by means of a cleaning and supply module, and the described transport procedure is performed until all the boxes of the at least two stacks are cleaned and optionally equipped with corresponding supply materials, by means of a cleaning and supply module.

A box ready for harvest, the readiness of a box for harvest being determined by means of a detection unit, during the cleaning and equipping with supply materials, is conveyed through the stack of boxes, located on the active chassis, by means of the downward vertical transporter, until it reaches the active chassis, the active chassis being deflected outwards. As a result, the box ready for harvest is unloaded onto the conveyor belt by the active chassis, by means of the downward vertical transporter.

Likewise, a new box comprising insects and supply materials, which is conveyed under the passive chassis by means of the conveyor belt, is loaded, through the passive chassis, by means of the upward vertical transporter, the passive chassis being deflected outwards by means of the box, upon loading, into the stack of boxes located on the passive chassis, such that automated insect breeding is carried out.

BRIEF DESCRIPTION OF THE DRAWINGS

The invention will be explained in greater detail in the following, with reference to an embodiment. In the drawings:

FIG. 8a is a perspective front view of the downward vertical transporter according to FIG. 1, having retracted lifting pins, FIG. 8b is a perspective front view of the downward vertical transporter according to FIG. 8a, having extended lifting pins, FIG. 8c is a perspective rear view of the downward vertical transporter according to FIGS. 8a and 8b, having extended lifting pins.

DETAILED DESCRIPTION OF THE PREFERRED EMBODIMENTS

Figure 1:
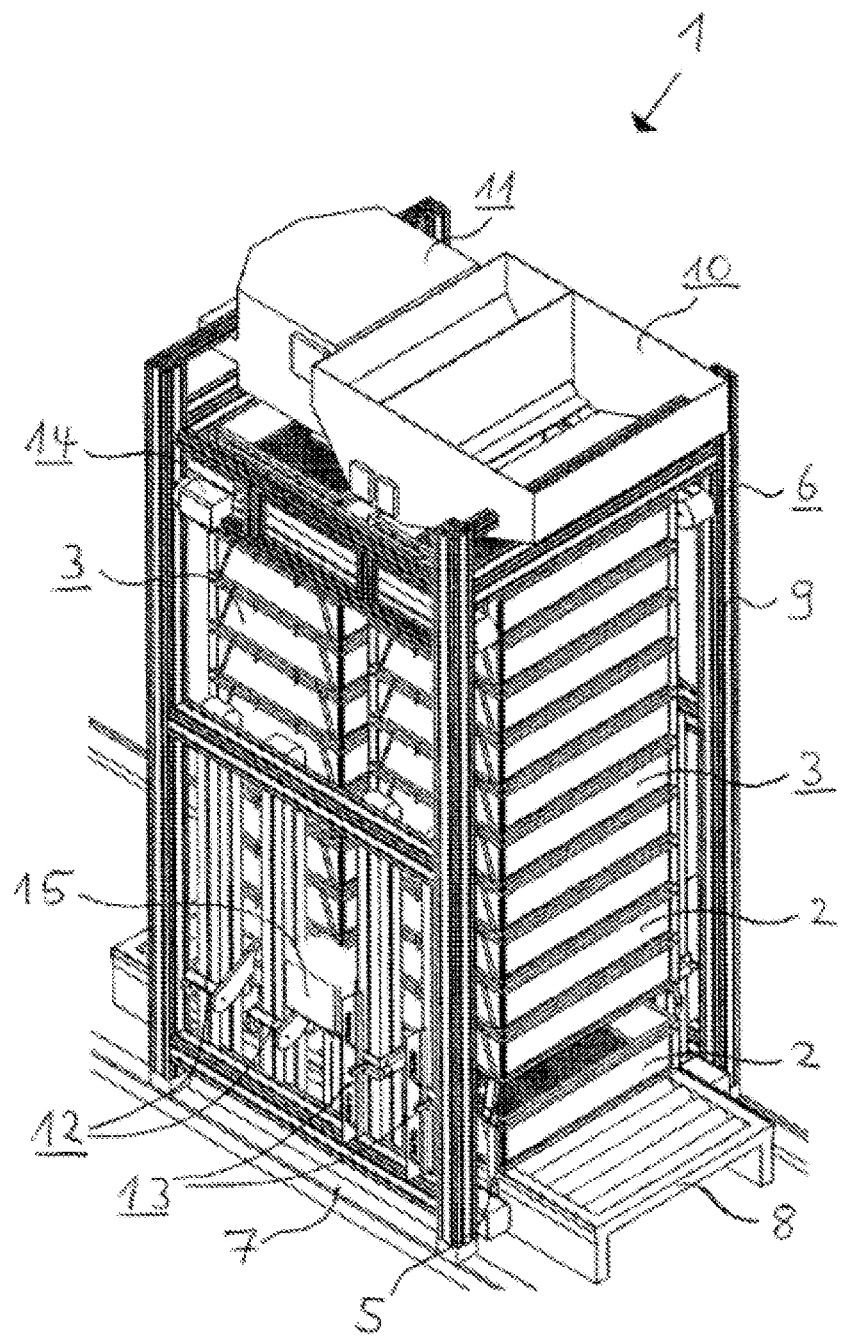
FIG. 1 is a perspective front view of the device comprising a gantry and two stacks of boxes containing insects.

FIG. 1 is a perspective front view of the device 1, comprising a gantry 6 having at least two stacks 3 of boxes 2, which are filled with insects. In this case, the gantry 6 consists of a profile system 9 and comprises a supply module 10, a cleaning module 11, an upward vertical transporter 12, a downward vertical transporter 13, an upper transverse transporter 14, a lower transverse transporter 15, an active chassis 5, a passive chassis 4 (not shown further here), as well as a conveyor belt 8 which is arranged between the chassis 4, 5, and a rail guide 7 along which the gantry 6 can be moved.

The stack 3 of boxes 2 on the passive chassis 4 can be lifted, at least by a box height, by means of the upward vertical transporter 12, the second box 2 from the bottom having previously being raised by the downward vertical transporter 13, such that the bottom box 2, located on the active chassis 5, can be brought, by means of the lower transverse transporter 15, under the stack 3 of the stack 3 raised upward by the upward vertical transporter 12.

Likewise, the uppermost box 2 of the stack 3 of boxes 2, the stack being raised by at least one box height by means of the upward vertical transporter 12, is brought, by means of the upper transverse transporter 14, from said stack 3 of boxes 2 over the stack 3 of boxes 2 of the stack 3 of boxes 2 conveyed downward by the downward vertical transporter 13.

In the case of transverse transport by the upper transverse transporter 14, the boxes 2 are in each case cleaned by the cleaning module 11 and supplied with necessary materials, in particular substrate and/or food, by the supply module 12.

A box 2 ready for harvest can be unloaded by the active chassis 5, by means of the downward vertical transporter 13, the active chassis 5 being deflectable outwards by servomotors 29 such that said box 2 arrives on the conveyor belt 8 located between the chassis 4, 5, such that the box 2 ready for harvest can then be transported away.

Likewise, the conveyor belt 8 can convey a fresh box 2 comprising new insects and substrate, as well as food, to the device 1, and the loading of the fresh box 2 through the passive chassis 4, by means of the upward vertical transporter 12, the lifting fingers 17 of the passive chassis 4 being deflectable outwards upon loading of the fresh box 2, is made possible.

Figure 2:
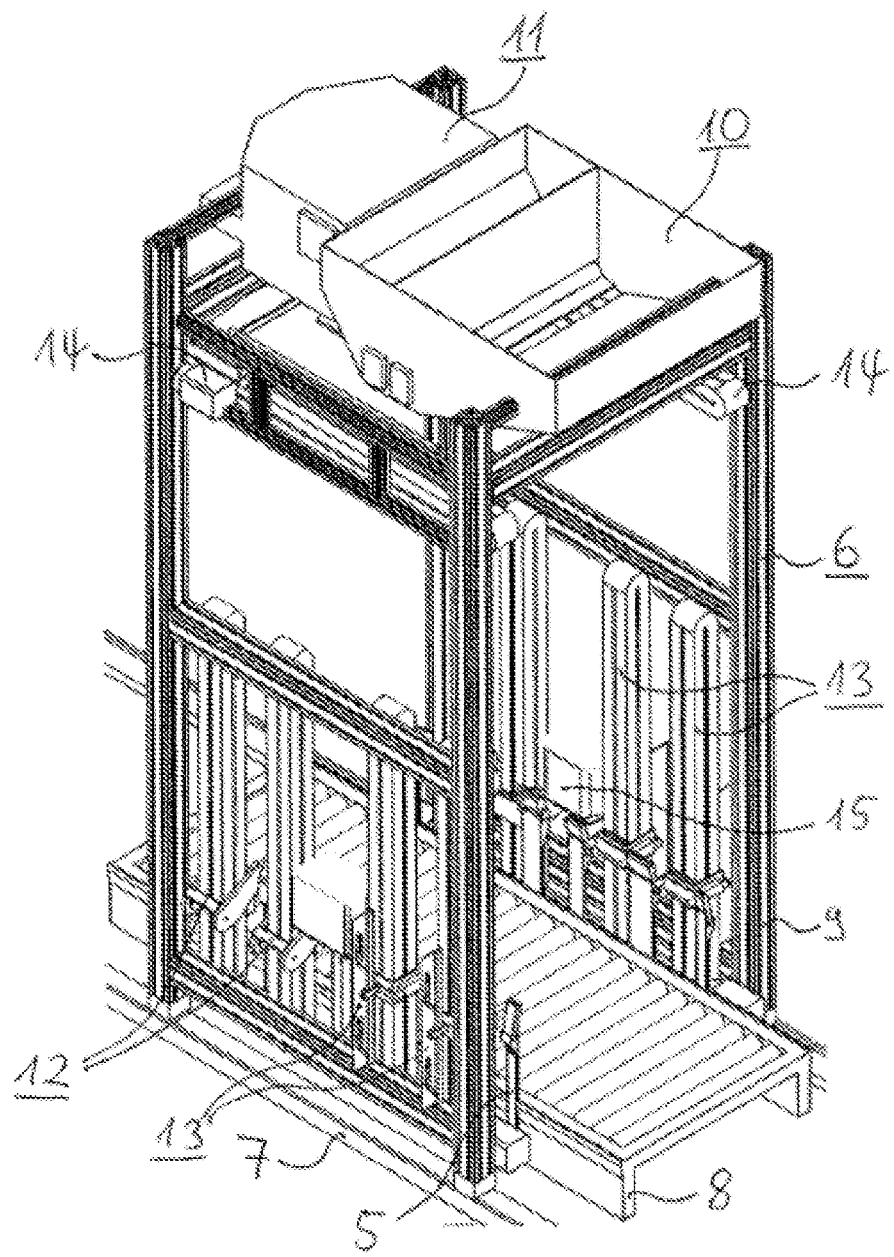
FIG. 2 is a perspective front view of the gantry according to FIG. 1 without the two stacks of boxes.

FIG. 2 shows the device 1 according to FIG. 1, but merely without the stack 3 of boxes 2 located on the passive 4 and active chassis 5. FIG. 2 shows the mutually opposing transport drives, i.e. the upward vertical transporter 12, the downward vertical transporter 13, the lower transverse transporter 15, and the upper transverse transporter 14, and also shows the conveyor belt 8 located between the chassis 4, 5, as well as the rail guide 7 on which the gantry 6 can be moved.

Figure 3A:
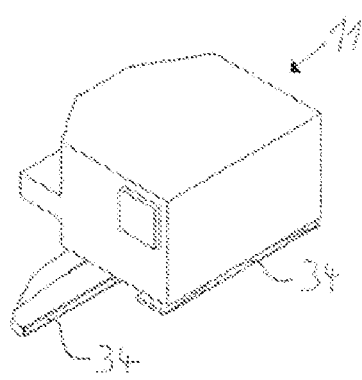
FIG. 3a is a perspective view from above of the cleaning module of the gantry according to FIG. 1.
Figure 3B:
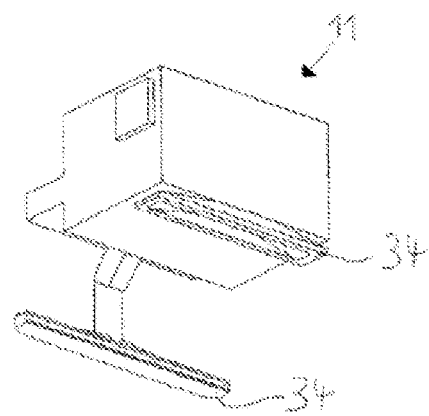
FIG. 3b is a perspective view from below of the cleaning module of the gantry according to FIG. 3a, FIG. 4a is a perspective view from above of the supply module of the gantry according to FIG. 1.

FIGS. 3a and 3b are perspective views from above and from below of the cleaning module 11 of the gantry 6 according to FIG. 1. In this case, the cleaning module 11 comprises two suction devices 34, one suction device 34 being attached laterally to the cleaning module 11, in order that this can be used for suctioning the waste, in particular the feces of the larvae, through a suction opening (not shown further here) of the boxes 2, and a further suction device 34 is attached under the cleaning module 11, such that said suction device 34 suctions the skins of the larvae out of the boxes 2 from above, in each case.

Figure 4A:
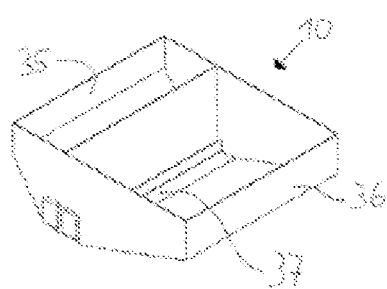
FIG. 4b is a cross-sectional view of the supply module of the gantry according to FIG. 4a, FIG. 5 is a perspective view of the passive chassis of the device according to FIG. 1.
Figure 4B:
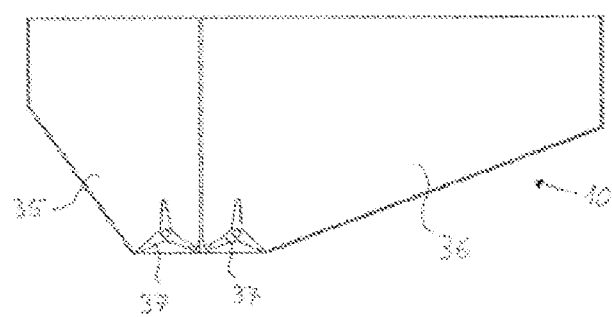

FIGS. 4a and 4b show the supply module 10 according to FIG. 1, in a perspective view from above and in cross section, the supply module 10 comprising two containers, at least one substrate container 35 and a food container 36, as well as one metering roller 37 arranged in each container. As a result of the advancement of the metering rollers 37 both in the substrate container 35 and in the food container 36, the correspondingly desired amount of the relevant material can be output from the supply module 10.

Figure 5:
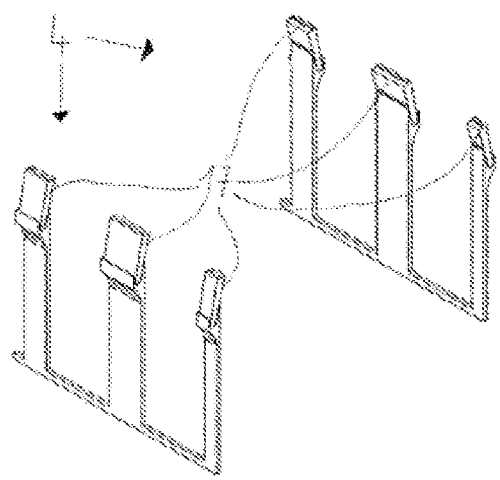

FIG. 5 is a perspective front view of the passive chassis 4 according to FIG. 1. The passive chassis 4 comprises a total of six lifting fingers 17, said lifting fingers 17 being passively deflectable towards the outside in the event of a fresh box 2 being loaded from below.

Figure 6A:
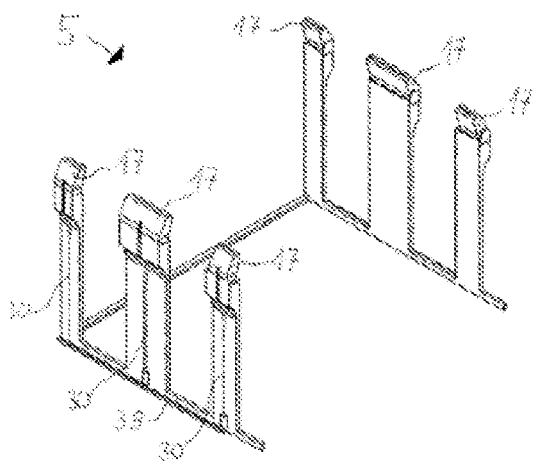
FIG. 6a is a perspective view of the active chassis of the device according to FIG. 1.
Figure 6B:
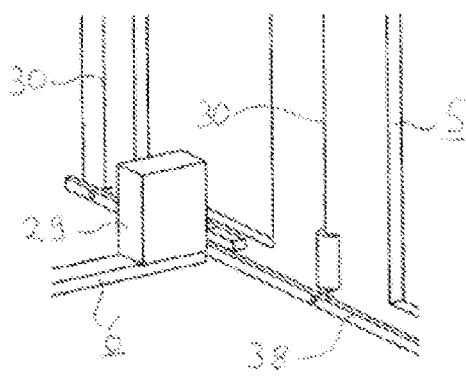
FIG. 6b is a perspective detailed view of the active chassis of the device according to FIG. 6a, including a servomotor of the gantry.

FIG. 6a is a perspective view of the active chassis 5 according to FIG. 1. The lifting fingers 17 of the active chassis 5 are connected by means of Bowden cables 30 to a web 38 of the active chassis 5. According to FIG. 6b, the lifting fingers 17 can be deflected outwards by actuating the web 38, in this case by pressing the web 38 downwards by means of a servomotor 29. Thus, a box 2 can be conveyed downward, through the active chassis 5, onto a conveyor belt 8 by means of the downward vertical transporter 13, following deflection of the lifting fingers 17 of the active chassis 5 by the servomotors 29, which are located on the gantry 6.

Figure 7:
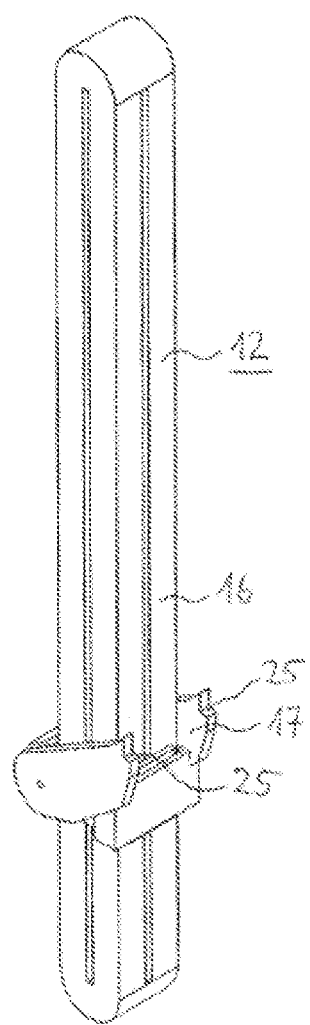
FIG. 7 is a perspective front view of the upward vertical transporter according to FIG. 1.

FIG. 7 shows one of four drive units of the upward vertical transporter 12 according to FIG. 1, said drive unit comprising a linear belt drive 16 and a lifting finger 17 having two lifting receptacles 25, the lifting finger 17 being deflectable towards the outside upon loading of a fresh box from below.

FIGS. 8a, 8b and 8c show one of four drive units of the downward vertical transporter 13, in a perspective front view in which the lifting pins 19 are retracted, in a perspective front view in which the lifting pins 19 are extended, and in a perspective rear view in which the lifting pins 19 are extended. FIG. 8a shows the lifting pins 19 guided by the lifting pin arm 18, said lifting pins 19 being connected to a roller 22 by means of a linear shaft 21, such that the lifting pins 19 are retracted by the roller guide 20.

FIG. 8b shows the lifting pins 19 which are extended on account of the roller guide 20 comprising deflection rockers 23, and the lifting pins 19 that are connected to a roller 22 by a linear shaft 21.

FIG. 8c is a perspective rear view of a drive unit of the downward vertical transporter 13 according to FIG. 8b. FIG. 8c shows that, when the lifting pin arm 18 of one drive unit of the downward vertical transporter 13 is moved down, the deflection rockers 23 are deflected such that the roller 22 which is connected to the lifting pins 19 via a linear shaft 21 is not deflected, such that the lifting pins 19 remain extended. Only when the lifting pin arm 18 is raised is the roller 22, which is connected to the lifting pins 19 by means of a linear shaft 21, deflected by the deflection rockers 23 of the roller guide 20 such that the lifting pins 19 are then retracted.

Figure 9:
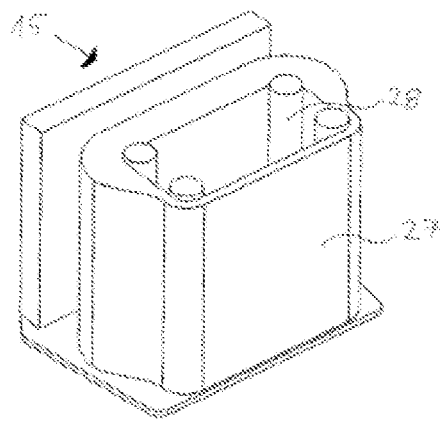
FIG. 9 is a perspective front view of the lower transverse drive according to FIG. 1.

FIG. 9 is a perspective front view of one of two drive units of the lower transverse transporter 15 according to FIG. 1. The one drive units of the lower transverse transporter 15 contains an asymmetrical belt 27 and a horizontal drive 28. Upon deflection of the asymmetrical belt 27 by the horizontal drive 28, a box 2 can be grasped by the thicker side of the asymmetrical belt 27 and can thus be conveyed in a direction, i.e. in the direction in which the horizontal drive 28 deflects the asymmetrical belt 27.

Figure 10:
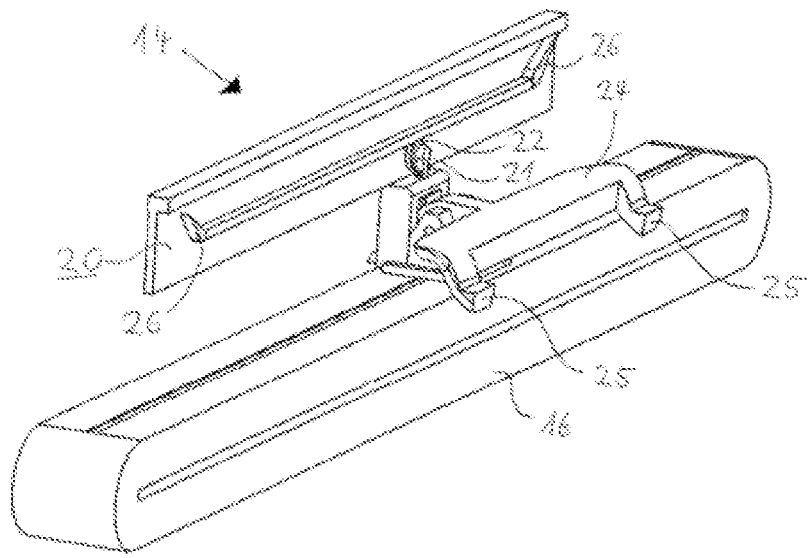
FIG. 10 is a perspective front view of the upper transverse drive according to FIG. 1.

FIG. 10 is a perspective front view of one of two drive units of the upper transverse transporter 14 according to FIG. 1. The drive unit of the upper transverse transporter 14 comprises a roller guide 20 having at least two rockers 26, a linear belt drive 16, a lifting arm 24 having at least two lifting receptacles 25, and a roller 22 which moves long the roller guide 20, the roller 22 being connected to the lifting arm 24 by means of a linear shaft 21.

If the lifting arm 24 has reached an end of the roller guide 20, and thus one of the rockers 26, the lifting arm 24 can be deflected by the roller guide 20, by means of the roller 22 which is connected to the lifting arm 24 by means of a linear shaft 21, such that a box 2 can be grasped by the linear belt drive 16 upon movement of the lifting arm 24. After a box 2 has been grasped, said box 2 remains grasped during the movement of the lifting arm 24 along the roller guide 20, until the next rocker 26. Upon reaching the next rocker 26, the lifting arm 24 is deflected by the roller 22 connected to the lifting arm 24 by means of a linear shaft 21, such that the box 2 can be deposited. The box 2 can thus be transported from left to right, or from right to left.

LIST OF REFERENCE SIGNS 1 device
2 box
3 stack
4 passive chassis
5 active chassis
6 gantry
7 rail guide
8 conveyor belt
9 profile system
10 supply module
11 cleaning module
12 upward vertical transporter
13 downward vertical transporter
14 upper transverse transporter
15 lower transverse transporter
16 linear belt drive
17 lifting finger
18 lifting pin arms
19 lifting pins
20 roller guide
21 linear shaft
22 roller
23 deflection rocker
24 lifting arm
25 lifting receptacles
26 rocker
27 asymmetrical belt
28 horizontal drive
29 servomotor
30 Bowden cable
34 suction device
35 substrate container
36 food container
37 metering roller
38 web

The invention claimed is:

1. A device for breeding, comprising
a plurality of individual boxes which are to be arranged in a stack comprising a plurality of planes of boxes, said boxes each being filled with larvae and substrate which contains food, and
an observation system for obtaining observable information relating to amount of the substrate and status of the insects in each individual box, in order to output instructions to breed further insects, or to harvest, or dispose of, the insects in the individual boxes, and
a food dispensing system adapted to dispense the food automatically and individually into the relevant box,
wherein the device comprises
at least one stack of boxes, which is located on a chassis, and a gantry, the gantry at least having a supply module, a cleaning module, an upward vertical transporter, a downward vertical transporter, an upper transverse transporter and a lower transverse transporter, and wherein a guide system is provided for moving the gantry to the at least one stack of boxes, and wherein a conveying system is provided for conveying boxes from and to the at least one stack of boxes and, using the gantry, for cyclical restacking, and supplying and cleaning of the insects within the boxes, within the at least one stack of boxes, and wherein the conveying system and the gantry are configured to load boxes into and unload boxes from the at least one stack of boxes, the supply module being divided into at least two containers, said containers each being equipped individually with at least one metering roller, at least one container being filled with substrate and at least one other container being filled with food, such that in the event of transport by the upper transverse transporter the substrate and subsequently food are dispensed into a box by an adjustable advancement of the at least one metering roller.

2. The device (1) according to claim 1, wherein the gantry (6) is constructed from a profile system (9) made of aluminum, and/or from a welded structure.

3. The device according to claim 1, wherein the upward vertical transporter of the gantry comprises opposingly, at least two drive units containing at least two linear belt drives and at least two lifting fingers on each drive, the lifting fingers being loadable during an upward movement, achieved by the drive, of the upward vertical transporter in order to absorb a weight, and wherein the lifting fingers are configured to be deflected outwards by insertion of a box from the conveyor belt through the passive chassis from below, in order to perform passively the hooking and unhooking for the transport of the boxes, by the upward vertical transporter.

4. The device according to claim 1, wherein the downward vertical transporter of the gantry opposingly, at least two drive units containing at least two linear belt drives and at least two lifting pin arms having at least two lifting pins connected to a roller, and a roller guide comprising deflection rockers configured to deflect the lifting pins of a lifting pin arm, connected to at least one roller, by a downward movement of the downward vertical transporter such that one box is held by the lifting pins, and said box is transported downward by the upward movement of the downward vertical transporter, the lifting pins connected to a roller being deflectable by a deflection rocker in the roller guide such that the downward vertical transporter is moved upward, without the lifting pins being extended, and thus no box is grasped, such that a further box by a linear belt drive, for the purpose of the downward movement of the downward vertical transporter, by the lifting pin arms and the lifting pins thereof that are connected to a roller, using the roller guide and the deflection rockers thereof.

5. The device according to claim 1, wherein the upper transverse transporter of the gantry comprises opposingly, at least one drive unit which a linear belt drive, a lifting arm having at least two lifting receptacles, a roller on the lifting arm which is coupled by means of a linear shaft, and a roller guide comprising at least two rockers, such that a movement of the lifting arm by a linear belt drive having a roller coupled via a linear shaft, along the roller guide, pivots the lifting arm out by a rocker on the roller guide such that a box is receivable and moveable from left to right and/or from right to left, such that at a further rocker of the roller guide a box, a lifting arm is deflected by a roller fastened to the lifting arm by a linear shaft, in order to deposit a box.

6. The device according to claim 1, wherein the lower transverse transporter of the gantry contains opposingly, a vertically oriented asymmetrical belt configured to be moved vertically by a horizontally oriented drive, the asymmetrical belt being of such a thickness, on one side, for grasping and moving a box from left to right and/or from right to left by horizontally oriented drive, on account of the vertical movement of the asymmetrical belt.

7. The device according to claim 1, wherein the gantry comprises servomotors, and wherein the active chassis contains a connection element fastened to the Bowden cables fastened to the lifting fingers, the connection element being actuatable by the servomotors on the gantry for deflecting the lifting fingers of the active chassis outwards by actuating the servomotors, so that a box that is ready for harvest is unloaded downward onto a conveyor belt, through the active chassis, by the downward vertical transporter (13).

8. The device according to claim 1, further comprising a detection unit in the gantry, wherein the detection unit comprises sensors and/or a camera, for determining the parameters required for insect breeding inside a box, and wherein a database is configured to compare the images acquired by the camera, which reproduce the status of supply materials for the insects in a box, with reference data, in order to determine the relevant status of supply materials for the insects inside a box, for use of the information thus obtained for machine learning.

9. The device according to claim 1, wherein each of the boxes comprises a double base and at least one suction opening between the bases, the upper base of the double base being constructed as a grating-like base, such that waste inside the box falls through said grating-like base, and the cleaning module is configured to remove said waste through the suction opening between the double base.

10. The device according to claim 9, wherein the cleaning module comprises at least first and second suction devices, wherein at least the first suction device is configured to suction the waste through the suction opening of a box, between the double base, and wherein at least the second suction device is configured to suction out during the transport by the upper transverse transporter and/or take up using electrostatics and/or remove by air separation the skins of the larvae as well as any food residues and other waste present inside the box.

11. The device according to claim 10, wherein the boxes comprise an RFID chip or another passive electronic chip, and/or a barcode, and/or a 2D matrix, for storing and retrieving data in order to carry out instructions based on the storable and retrievable data.

12. The device according to claim 1, wherein a station is present for the gantry, in order to empty the cleaning module, and wherein the containers of the supply module are configured to be refilled with materials.

13. The device according to claim 1, wherein the stacks of boxes are configured to be lined up one behind the other, lengthways, as often as desired, and wherein said stacks of boxes lined up lengthways are configured to be lined up side-by-side, in order to optimally adapt the device to the local conditions in-order to make optimum use of the local conditions.

14. The device according to claim 13, wherein at least one conveyor belt is arranged orthogonally to the stacks of boxes in order to supply said stacks of boxes with new boxes comprising insects and supply materials from a store, and wherein said at least one conveyor belt is configured to transport boxes ready for harvest away from the stacks of boxes and into a store.

15. A method having the device according to claim 1, the method comprising:
   raising the lowest box of the stack, which is located on the passive chassis, by at least one box height, using the upward vertical transporter, at the same time, the downward vertical transporter raises the second box from the bottom, from the stack of the active chassis, such that the bottom box of the stack on the active chassis is brought, using the lower transverse transporter, under the stack raised by the upward vertical transporter, and
   moving the second from bottom raised box, using the downward vertical transporter, by at least one box height, the uppermost box of the stack, which is raised by one box height, by the upward vertical transporter, likewise being brought over the stack of boxes, located on the active chassis, by an upper transverse transporter, during the transport of the box by the upper transverse transporter, the box comprising insects and the supply materials thereof being cleaned, and optionally equipped with corresponding supply materials, by a cleaning and supply module, and
   performing the described transport procedure until all the boxes (2) of the stacks on the passive chassis and the active chassis are cleaned and optionally equipped with corresponding supply materials, by a cleaning and supply module, and
   conveying a box ready for harvest, the readiness of a box for harvest being determined using a detection unit, during the cleaning and equipping with supply materials, through the stack of boxes, located on the active chassis, by the downward vertical transporter, until the box reaches the active chassis, the active chassis being deflected outwards, such that the box ready for harvest is unloaded onto the conveyor belt, through the active chassis, by the downward vertical transporter, and
   loading a new box comprising insects and supply materials, which is conveyed under the passive chassis by the conveyor belt, through the passive chassis by the upward vertical transporter, the passive chassis (4) being deflected outwards by the box, upon loading, into the stack of boxes located on the passive chassis, such that automated insect breeding is carried out.

* * * * *